(12) United States Patent
Gillick et al.

(10) Patent No.: US 6,599,296 B1
(45) Date of Patent: Jul. 29, 2003

(54) RATCHETING HANDLE FOR INTRALUMINAL CATHETER SYSTEMS

(75) Inventors: Matthew J. Gillick, Murrieta, CA (US); Christopher J. Tarapata, North Andover, MA (US); Christopher A. Stout, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/917,189

(22) Filed: Jul. 27, 2001

(51) Int. Cl.[7] ............................................. A61B 17/00
(52) U.S. Cl. ................................................. 606/108
(58) Field of Search .......................... 606/108, 191, 606/198; 604/528

(56) References Cited

U.S. PATENT DOCUMENTS

| | | | | |
|---|---|---|---|---|
| 4,921,484 A | * | 5/1990 | Hillstead | 604/104 |
| 4,994,065 A | * | 2/1991 | Gibbs et al. | 606/92 |
| 5,275,151 A | * | 1/1994 | Shockey et al. | |
| 5,415,664 A | * | 5/1995 | Pinchuk | 606/108 |
| 5,433,723 A | * | 7/1995 | Lindenberg et al. | 606/198 |
| 5,591,172 A | * | 1/1997 | Bachmann et al. | 606/108 |
| 5,788,710 A | * | 8/1998 | Bates et al. | 606/127 |
| 5,833,694 A | * | 11/1998 | Poncet | 606/108 |
| 5,944,727 A | | 8/1999 | Ahari et al. | 606/108 |
| 5,968,052 A | | 10/1999 | Sullivan, III et al. | 606/108 |
| 6,402,760 B1 | * | 6/2002 | Fedida | 606/108 |

* cited by examiner

Primary Examiner—Ralph A. Lewis
(74) Attorney, Agent, or Firm—Fulwider Patton Lee & Utecht, LLP

(57) ABSTRACT

A ratcheting handle actuator provides for a tool to actuate an intraluminal catheter system for treatment at an intraluminal site by repeated movements of the handle. This allows for actuation over a greater distance than a physician might be able to perform in a single motion while preserving a direct correspondence between the movements of the ratcheting handle and the actuation of the intraluminal device.

20 Claims, 4 Drawing Sheets

RATCHETING HANDLE FOR INTRALUMINAL CATHETER SYSTEMS

BACKGROUND OF THE INVENTION

The present invention relates to intraluminal catheters and devices. More specifically, the present invention relates to a device for actuating an intraluminal device. Intraluminal catheters and devices are currently employed in a variety of medical procedures. These procedures often require manipulation (or actuation) of the intraluminal device by a mechanism located outside of the patient's body. This invention relates to such devices which may be employed in a number of such procedures.

Catheters have long been used in intraluminal procedures for various medical needs. They generally are made from elongated tubes which may be placed within various body lumens. A common use for catheters is the treatment of vascular diseases. In such treatment, a catheter is inserted into a body vessel such as an artery. The catheter is then advanced through the artery to the site of the disease where treatment is performed.

A wide variety of treatments are currently available using different devices and mechanism delivered with or within, such catheters. For example, a stent or graft may be delivered to the site of a diseased artery and deployed within the artery. Other treatments employ the expanding of balloons (as in angioplasty) or delivery of drugs to treat arteries. Importantly, the treatment at the intraluminal site typically requires the manipulation of the catheter system external to the patient's body. That is, a physician-operator must actuate the catheter system into performing the intraluminal treatment by the use of devices which remain outside the patient's body. These devices are connected to the catheter system and are able to perform the treatment at the intraluminal site.

Certain medical terms regarding the orientation of medical devices are useful for a complete understanding of these devices. The term "distal" typically refers to a direction away from the operator of the device. Thus, the distal end of the catheter is inserted into the body and advanced distally through the vascular system. The term "proximal" typically refers to a direction towards the operator of the device. Thus, the proximal end of the catheter remains outside of the body and the catheter is withdrawn proximally to be removed from the body. These terms will be used herein for consistency.

An example of a known intraluminal procedure is the delivery of a self-expanding stent to the site of a stenosis (the narrowing of an artery due to vascular disease). Self-expanding stents typically employ spring forces which expand the stent radially outward to contact the arterial wall and maintain the arterial lumen in an expanded state. Typically, such a stent is mounted onto a catheter, collapsed to a smaller diameter and contained within a sheath for delivery. For deployment, the physician-operator may retract the sheath to expose the stent to allow it to expand for treatment. This may be accomplished by using a variety of actuator mechanisms connected to the proximal end of the catheter.

The actuator mechanism may be as simple as a knob independently attached to the catheter sheath. As the physician-operator pulls the knob proximally, the sheath withdraws proximally. Such a direct connection usually allows the physician some amount of control over the intraluminal procedure. Therefore, a direct controlling mechanism for performing the intraluminal procedure may be a preferred aspect of a catheter system.

As in the example described above, some intraluminal procedures require the retraction of sheaths, wires and the like while the main catheter remains stationary. Some procedures also require the advancement of similar devices. Simple solutions have been developed, such as attaching a knob, pull, or lever to the device requiring advancement or withdrawal. This allows some direct control by the physician-operator within, of course, certain limits.

One limitation in the use of a direct control device has been the distance required for advancing or retracting the device. As the distance increases, direct control of the device may become awkward or cumbersome. That is, a physician-operator may find it difficult to manipulate the control device over several inches while maintaining the remainder of the catheter system stationary.

Solutions to this problem include the use of pistol-grip handles with ratchet triggers. When one squeezes the trigger, the catheter system is actuated a certain distance, whereas releasing the trigger does not cause any further actuation. Thus, the catheter system can be repeatedly actuated in a single direction by repeatedly squeezing and releasing the trigger. These devices, however, do not provide direct control of the procedure. The squeezing of the trigger usually does not impart movement in the intraluminal device in one-to-one correspondence. Thus, a triggering mechanism inherently replaces the direct control by the physician with a mechanical relaying of control.

What has been needed is a mechanical device which allows direct manipulation of an intraluminal medical device that requires a lengthy displacement. The present invention satisfies these and other needs.

SUMMARY OF THE INVENTION

The present invention relates to a device for actuation of an intraluminal catheter system. More precisely, the present invention consists of a ratcheting handle which enables the actuation of an intraluminal catheter system in a direct correlation of transmitted motion, even when a large relative motion is required. The present invention includes a stationary base, a slidable pull back trigger or handle, a ratcheting system and a connection to the catheter system to create an overall intraluminal catheter system.

The present invention may enable actuation of a variety of intraluminal catheter systems. These systems, in turn, provide a variety of treatments. Known intraluminal treatments include, among others, vessel occlusion, angioplasty and the implantation of stents and grafts. Stents are intraluminal prosthesis which are implanted to expand and maintain the patency of body vessels. Grafts are also intraluminal prosthesis which may be used to replace body vessels or to isolate diseased vessels from the flow of blood.

Intraluminal treatments typically require actuation of the catheter system for treatment. For instance, in the implantation of a self-expanding stent, a sheath may be required to be retracted to allow the delivered stent to expand. When a particularly long stent is to be implanted, the sheath may be required to be retracted a greater distance than a physician-operator feels comfortable retracting in a single motion. The present invention provides a device to retract a sheath the required distance without requiring excessive manipulation by the physician-operator.

The present invention is configured to allow direct manipulation of the catheter system without a mechanical interface. Direct manipulation of the catheter system usually allows the physician the maximum amount of control over the intraluminal procedure. Thus, in the example described above, in which a sheath is retracted, the device of the present invention enables the physician to perform the procedure at an intraluminal site with directly corresponding motions. That is, as the physician withdraws the slidable pull-back trigger along the base, the sheath is retracted a corresponding distance at the intraluminal site. Since this device is in-line with, and directly connected to, the catheter system, the physician's motions directly correspond to the motion of the sheath.

The present invention also permits the direct actuation of catheter systems when the required retraction or motion is greater than a physician may feel comfortable in performing in a single motion. Thus, in the example of the delivery of a long self-expanding stent, the present invention permits the direct manipulation of the retractable sheath albeit in multiple motions. In such a procedure the physician may withdraw the pull-back trigger the length of the base, which may only correspond to a portion of the motion required to withdraw the sheath to expand the stent. The physician may then advance the pull-back trigger, leaving the remainder of the catheter system, including the sheath, stationary. The physician may then withdraw the pull-back trigger again which withdraws the sheath an equivalent amount. This procedure may be repeated multiple times until the sheath is fully withdrawn and the stent expanded. Although reference herein is made to the withdrawal of a sheath for the deployment of a self-expanding stent, those of skill in the art will recognize that this device can be capable of performing a variety of functions with other medical devices and in other medical procedures.

The base of the present invention connects to the catheter system in a fixed manner. The proximal end of the catheter connects directly to the distal end of the base. The physician may use the base to advance or withdraw the catheter system within the patient's body. The base may be further configured to provide for the functions of the catheter system. For example, the base may include a guide wire port on the distal end of the base which provides access for a guide wire extending through the base and catheter system. The base may also include flush ports for flushing the system, and thumb-rests to facilitate manual actuation of the catheter system. Furthermore, the bottom side of the base may be configured to securely rest on a curved surface such as a patient's leg, for example, when a femoral approach is used.

An actuating device is slidably disposed within the base. This actuating device includes the pull-back trigger and a set of ratchet teeth. The pull-back trigger (or simply the "pull") may be alternatively configured as a knob, a trigger, a lever or simply as a bar. Even though the term "pull-back trigger" is used herein, it should be recognized that this actuating device may also be pushed or slid in some other manner. The operative requirement of the pull-back trigger is that it can be manually grasped for sliding both proximally and distally along the base. Furthermore, the actuating device may include a pair of pull-back triggers which will allow the physician-operator to use two or more fingers to operate the device.

A set of ratchet teeth is connected to the pull-back trigger such that they slide proximally and distally with the pull-back trigger. If the desired function of the device is the proximal withdrawal of some article (such as a sheath) the teeth should face proximally. To face proximally, the ratchet teeth each have a sloping surface and a proximal facing horizontal surface. This horizontal surface is configured to engage a corresponding surface of distal facing ratchet teeth. The sloping surface is configured to slide over the corresponding surfaces of distal facing ratchet teeth. If the desired function of the device is the distal advancement of some article, then the teeth should face distally with the surfaces reversed.

A slider mechanism is also disposed within the base and includes at least on ratchet tooth correspondingly engaged with the set of ratchet teeth on the actuating device. The slider is connected to that portion of the intraluminal catheter system that is actuated. Thus, in the example described above, the slider attaches directly to the sheath.

The slider, actuating device and base may be configured such that the actuating device is withdrawn as the slider is withdrawn. Since the slider is directly connected to the part of the catheter system requiring actuation, that part of the system is likewise withdrawn. Due to the configuration of the ratcheting teeth, the slider is not advanced as the actuating device is advanced. Thus, through repetitive withdrawing and advancing of the actuating device the slider can be withdrawn repeatedly without being advanced. This, in turn, actuates the movable portion of the catheter system in discreet steps, which can be repeated to actuate that portion a greater distance than one motion might allow.

The base may also include a separate top portion which covers at least the slider and ratcheting teeth of the actuating device. The top portion may be fixedly secured to the base so that the top does not move with either the slider or actuating device. Furthermore, the top portion may include a set of ratcheting teeth with the same orientation as those on the actuating device. When combined with at least one corresponding tooth on the top of the slider, this set of ratcheting teeth securedly prevent the slider from advancing distally as the actuating device is advanced.

A slot may be included through the top portion to allow visualization of the slider. In this manner, the physician-operator may monitor the amount of withdrawal or advancement of the actuating portion of the catheter system. The slot may also be used to manually depress the slider to disengage the ratcheting teeth of the slider and top portion. When the slider is disengaged from the top portion, the slider and actuating device may be advanced forward in unison, thus allowing a motion of the slider which is otherwise precluded by the ratcheting system. This may be useful, for example, in repositioning a sheath after it has been partially withdrawn.

The advantages of the present invention will become apparent from the following detailed description thereof when taken in conjunction with the accompanying exemplary drawings. Those of skill in the art will recognize that variations are possible to the described preferred embodiments while remaining within the scope of the invention. Thus, the following descriptions are not intended to limit the scope of the invention which is to be defined by the claims.

DETAILED DESCRIPTION OF THE PREFERRED EMBODIMENTS

The present invention relates to a handle device for actuating an intraluminal catheter. More specifically, the invention relates to a handle including a ratcheting actuator which permits repeated actuation of the catheter system in a single direction. This permits a physician to manually and directly actuate a catheter system through a larger distance than is efficient to perform in a single step. The present invention is also part of the catheter system described.

The present invention is therefore advantageous in the deployment of long (greater than 80 mm) self-expanding stents using one hand. Whereas the human hand is limited in the length of stroke it can provide to actuate a stent deployment device, the present invention is configured to enable one-handed deployment of long stents by means of a ratcheting mechanism. The ratcheting mechanism provides for two or more pulls of an actuating handle to actuate the stent deployment device over such greater lengths. This configuration maintains the 1:1 ratio of hand movement to stent deployment preferred by physicians.

Figure 1:
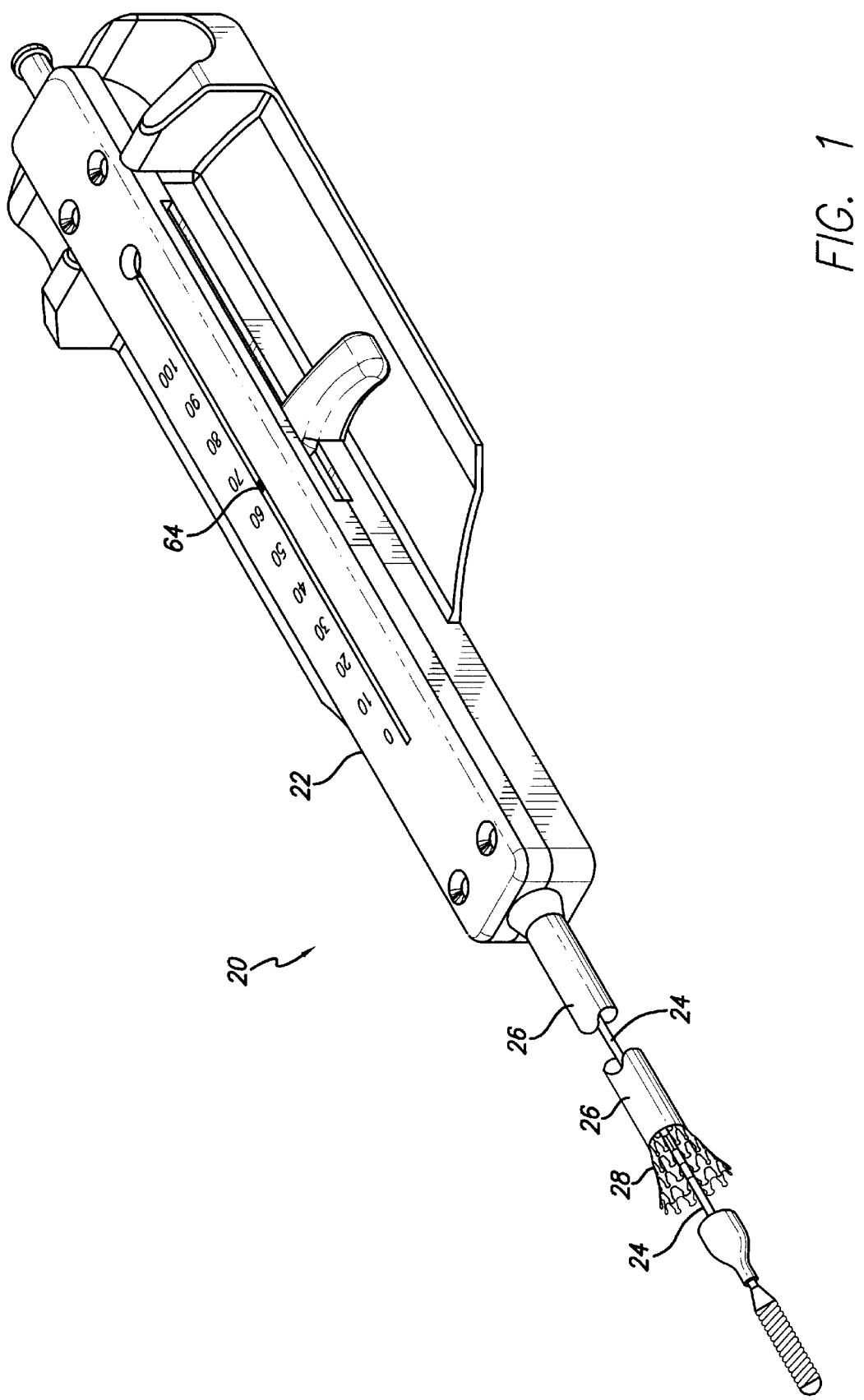
FIG. 1 is a perspective view of an embodiment of a catheter system.

FIG. 1 depicts a catheter system 20 conforming to an embodiment of this invention. The example depicted includes an actuating handle 22, a catheter 24, a sheath 26 and a stent 28. The sheath is shown partially withdrawn such that the stent is partially deployed. In general, this type of catheter system may be useful in the treatment of a variety of vascular diseases.

Intraluminal procedures and treatments are known in the medical arts. As examples, the types of treatments which may benefit from the improvements of the present invention include: the delivery of long self-expanding stents, as may be required in the femoral or carotid arteries; and the delivery of long grafts to treat aneurysms such as abdominal aortic aneurysms. These and other treatments may benefit from the present invention in terms of facilitating deployment of the intraluminal devices.

Figure 2:
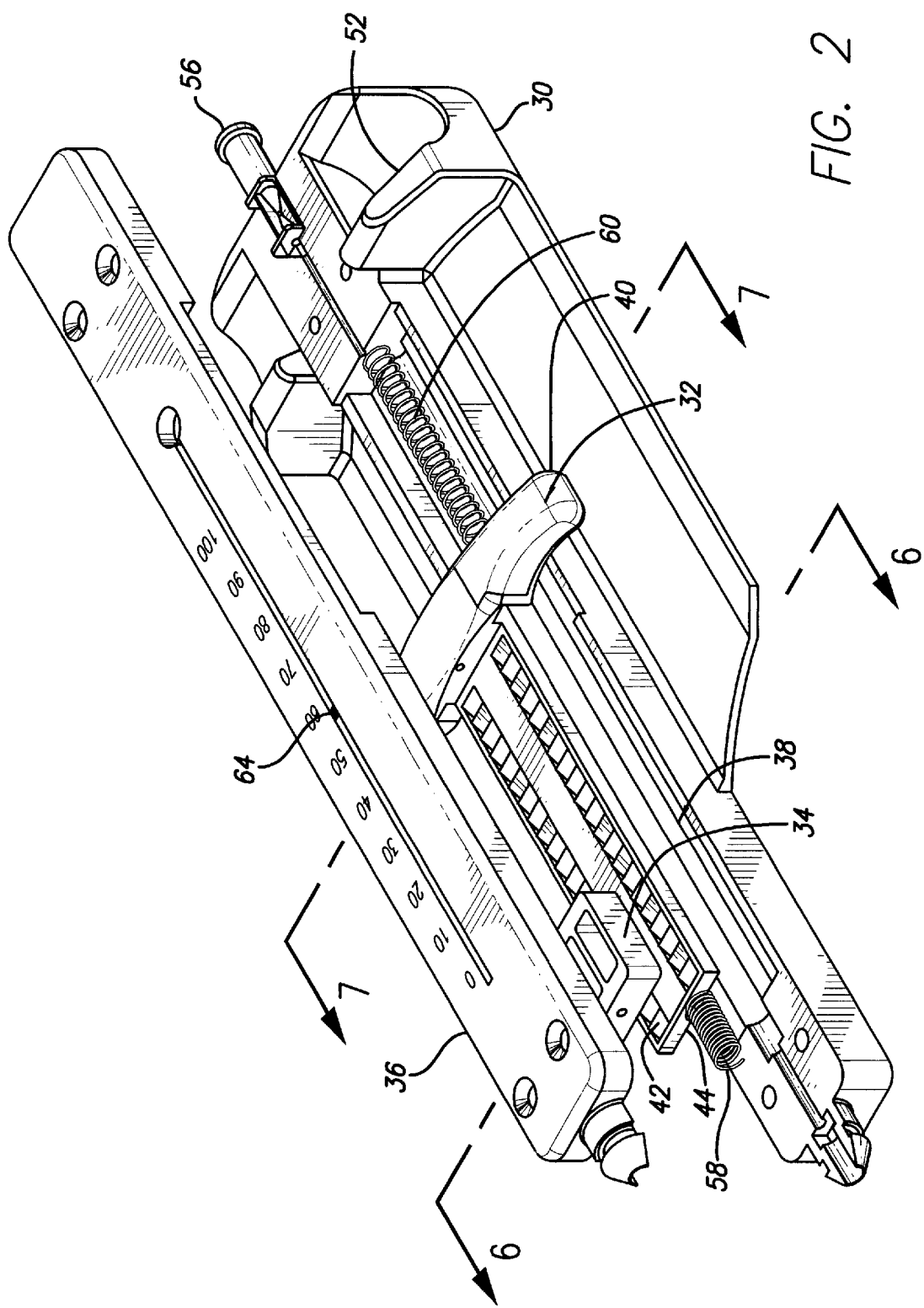
FIG. 2 is an exploded perspective view of an embodiment of a catheter actuating handle.

FIG. 2 depicts an embodiment of the actuating handle 22. This example includes a base 30, an actuating device 32, a slider 34 and a top 36 as major components. The base may include a groove 38 extending proximally and distally. The groove is configured to at least partially enclose the actuating device and enable the sliding engagement between the actuating device and the base. The top of the actuating handle forms a cover and encloses at least the slider and the actuating device. The top and the base may be fixedly secured by any number of conventional securing means such as the use of screws or bolts as fasteners or gluing.

Figure 4:
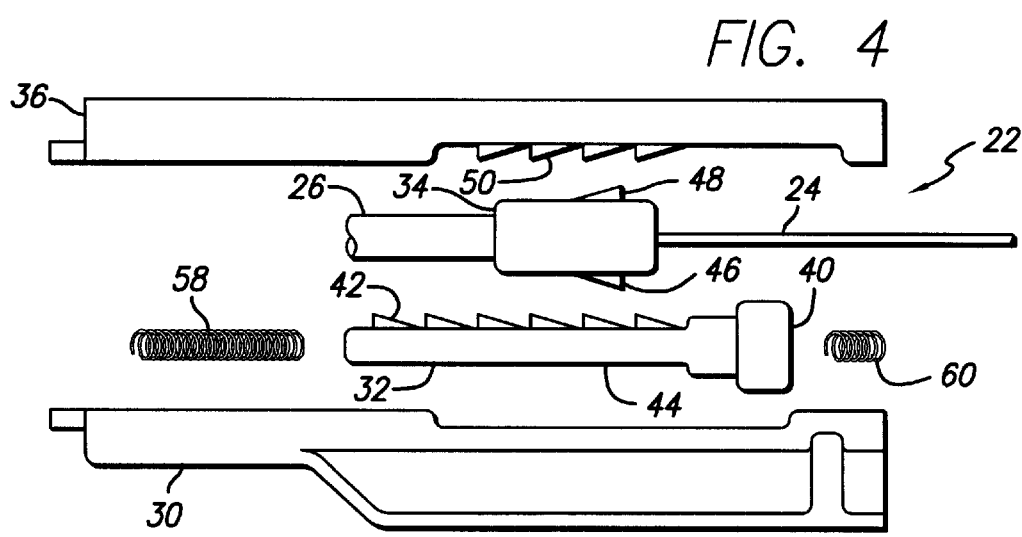
FIG. 4 is an exploded perspective view of an embodiment of a catheter actuating handle.

The ratcheting function of the actuating handle 22 is primarily enabled by the actuating device 32, the slider 34 and the top 36. The actuating device includes at least a pull-back trigger 40 and a plurality of ratcheting teeth 42. The pull-back trigger may be configured for pushing or pulling and enables manual manipulation of the actuating device. Thus, a physician uses the present invention by pushing and pulling on the pull-back trigger. The ratcheting teeth each include a sloping face and a horizontal face. The orientation of these faces determines the direction in which the actuating handle actuates the catheter system. In the example of FIG. 2, the horizontal face of each tooth faces proximally, indicating the actuating handle is configured to actuate the catheter system 20 proximally ("retracting" or "withdrawing"). In the example of FIG. 4, the horizontal face of each tooth faces distally, indicating the actuating handle is configured to actuate the catheter system distally ("advancing"). The plurality of ratcheting teeth are disposed on a rack 44 attached to the pull-back trigger.

Figure 3:
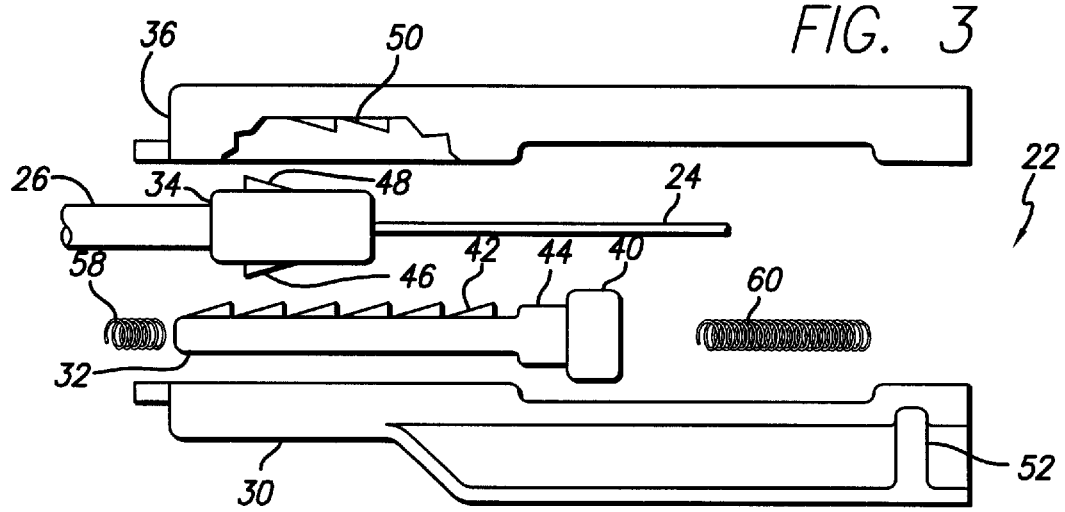
FIG. 3 is an exploded side view of the catheter actuating handle depicted in FIG. 2.

The slider 34 is disposed between the rack 44 of the actuating device 32 and the top 36 of the actuating handle 22. The slider slides over the rack and the top. The slider also includes at least one ratcheting tooth 46 (shown in FIG. 3) engaging the plurality of ratcheting teeth 42 on the actuating device. This ratcheting tooth (or teeth) may be of the same configuration as the teeth on the actuating device except in the opposite orientation. Thus, in the example depicted in FIGS. 2 and 3, the slider withdraws proximally as the actuating device is retracted, yet remains stationary by sliding over the rack as the actuating device is advanced. The slider may also include at least one ratcheting tooth 48 configured to engage with a plurality of ratcheting teeth 50 (shown in FIG. 3) disposed on the top. The plurality of ratcheting teeth on the top are of the same orientation as the plurality of ratcheting teeth on the actuating device. Furthermore, the ratcheting teeth on the slider engaging the top are of the same orientation as the ratcheting teeth engaging the actuating device. In the configuration depicted in FIGS. 2 and 3, the slider is prevented from moving distally as the actuating device slides distally.

Figure 5:
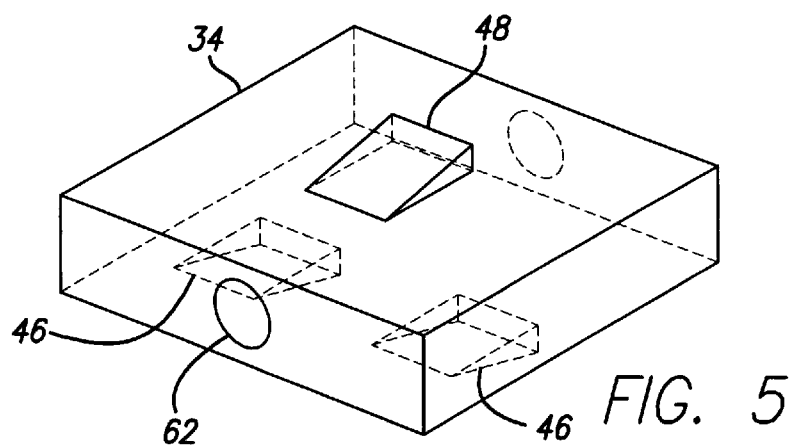
FIG. 5 is a transparent perspective view of a slider mechanism.
Figure 6:
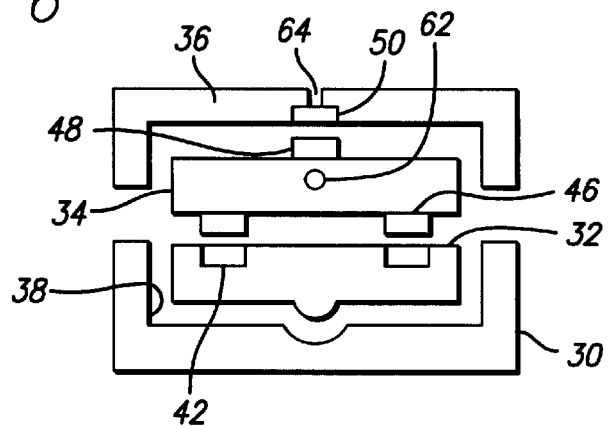
FIG. 6 is an exploded cross-sectional view of the catheter system of FIG. 2 taken along line 6—6.

As depicted in FIG. 5 the slider 34 may be configured with a variety of ratcheting teeth arrangements. Those on the top surface of the slider are arranged to engage with the plurality of ratcheting teeth 50 on the top 36. Those ratcheting teeth on the bottom surface of the slider are arranged to engage the plurality of ratcheting teeth 42 on the actuating device 32. As depicted in FIG. 6, the slider itself is disposed between the top and the actuating device in such a manner as to allow the slider to slide along both. The slider is further configured to include engagement with the catheter system 20. This may be as simple as a channel 62 disposed throughout the slider. This engagement allows an affixed connection with the portion of the catheter to be actuated and a slidable connection with the stationary portion.

Figure 7:
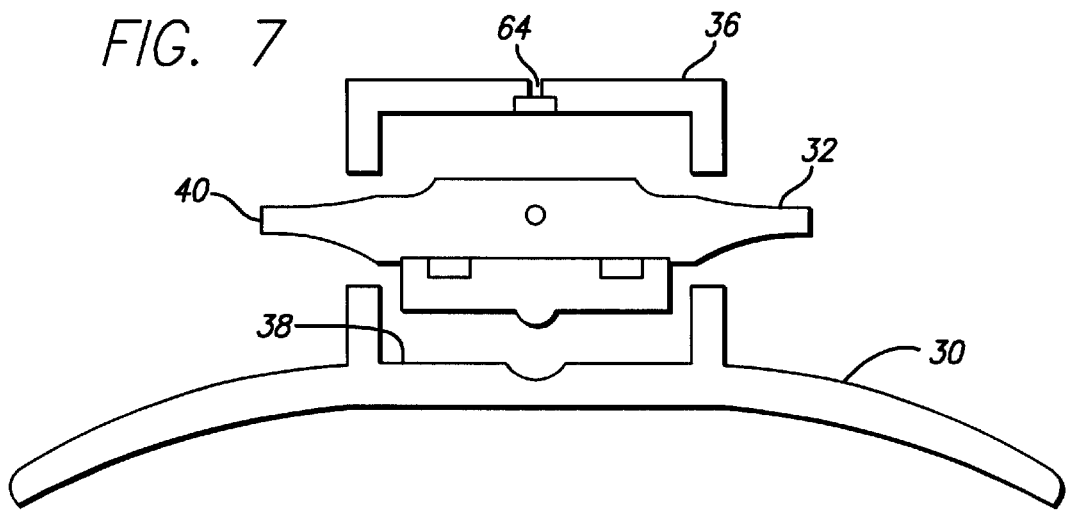
FIG. 7 is an exploded cross-sectional view of the catheter system of FIG. 2 taken along line 7—7.

As depicted in FIGS. 6 and 7 the actuating device 32 is typically enclosed by the top 36 and the base 30, except for the pull-back trigger 40 which extends outward. The actuating device is disposed therein in such a manner as to allow it to slide both distally and proximally as the pull-back trigger is manipulated. This may be accomplished simply by ensuring a close fit between all the members without fixation, except between the top and the base.

A distal spring 58 may be mounted between the base 30 and the distal end of the actuating device 32. This spring may be configured to mechanically assist the retraction of the actuating device. While the actuating device is disposed proximally on the base the distal spring is compressed and tends to force the actuating device distally. Thus, less force is required for the physician to retract the actuating device. This is particularly useful in sheathed catheter systems where additional force is initially required to retract the sheath from the fully closed (sheathed) condition.

A proximal spring 60 may be mounted between the base 30 and the proximal end of the actuating device 22. This spring may be configured to bias the actuating device into a distal position. In such a configuration, the physician would not be required to manually advance the finger pull 40 after retraction. The physician would release the finger pull and allow the proximal spring to return the actuating device into the distal position. By reversing the orientation of the actuating device (that is, orienting the ratcheting teeth to advance the catheter system, as in FIG. 4) the functions of the distal spring 58 and proximal spring 60 would also be reversed.

The catheter 24 of the catheter system 20 connects directly to the actuating handle 22. That portion of the catheter system 20 requiring actuation (such as sheath 26) connects to the slider 34. Thus, when the physician withdraws the actuating device, the slider retracts the sheath. Since the actuating device 32 can be independently advanced, the physician can repeatedly withdraw the actuating device to retract the sheath a greater distance than the physician may be able to perform in a single motion.

Figure 8:
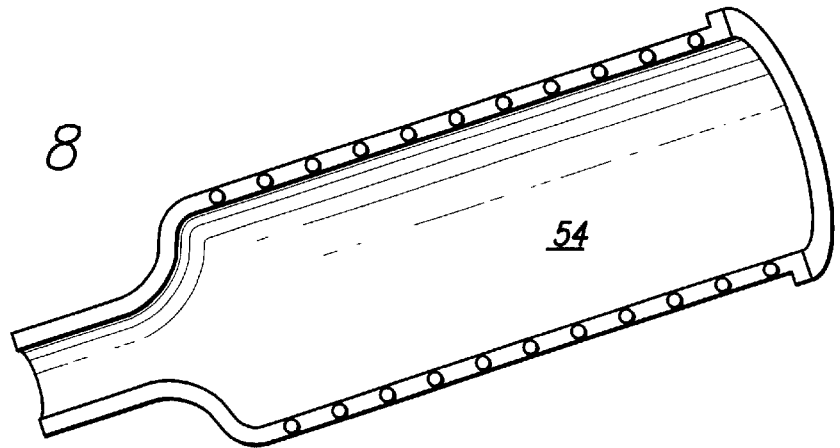
FIG. 8 is a bottom view of the catheter actuating handle depicted in FIG. 2.

The base 30 may be further configured to facilitate the physician's use. The base may include thumb-rests 52. The physician places his thumb on one of the thumb-rests and his finger on the pull-back trigger 40. By squeezing his thumb and finger together, the physician thereby retracts (or withdraws) the actuating device 32. Further improvements include a rounded bottom surface 54 which enables the base to be securely rested upon a patient's leg, as depicted in FIG. 8. This may be useful in a femoral approach wherein the thigh is the site of the incision and access for the catheter system.

The top 36 of the actuating handle 22 may also be further configured to facilitate the physician's use. Specifically, a slot 64 may be disposed through the top along the path of the slider 34. This permits the physician to see the position of the slider which indicates the corresponding position of the moveable portion of the catheter system 20. With a wide slot the physician may depress the slider with a tool or a finger to disengage the ratcheting teeth 48 on the top surface of the slider from the plurality of ratcheting teeth 50 on the top. By continuing to depress the slider the physician may be able to actuate the slider in the direction prohibited by the plurality of ratcheting teeth on the top.

The catheter system 20 may also comprise an access port 56 at the proximal end of the actuating handle 22. A guide wire (not shown) may access the entire catheter system 20 through such an access port. The access port may also be used to flush the entire catheter system. Flushing consists of forcing liquid through the system to evacuate air prior to intraluminal insertion of the system.

Locking mechanisms (not shown) may also be included with the catheter system 20. Such a mechanism holds the actuating device 32 firmly in place until the physician is prepared to perform the intraluminal procedure by actuating the system. Such a mechanism prevents premature deployment and may be as simple as a latching pin or a rotating lock.

The actuating handle 22 as well as its components may be formed of a hard plastic suitable for medical use. The plastic may be molded by any conventional method which is known in the art to produce products of medical quality.

Although the invention has been described above for use in a few exemplary intraluminal procedures, those of skill in the art will readily recognize that the present invention may be used in a variety of procedures. Furthermore, various modifications and additions may be made to the device described herein without evading the scope of the invention. Thus, the scope of the invention is intended to be limited only by the following claims:

What is claimed is:

1. A device for actuating an intraluminal catheter, comprising:
   a handle base;
   an actuator slidably engaged with the handle base such that the actuator may be withdrawn or advanced; and
   a slider in ratcheted engagement with the actuator and adapted to be connected to an intraluminal catheter;
   wherein the ratcheted engagement between the actuator and slider allows the slider to be repeatedly withdrawn or advanced which actuates the catheter in a single direction and the handle base includes a top portion disposed over the slider and a plurality of ratcheting teeth disposed on the top portion, at least one ratcheting tooth on the slider engaging the plurality of ratcheting teeth on the top portion.

2. The actuating device of claim 1, wherein the actuator includes at least one knob.

3. The actuating device of claim 1, wherein the actuator includes a plurality of ratchet teeth.

4. The actuating device of claim 1, wherein the handle base is configured to securely attach to a catheter.

5. The actuating device of claim 1, wherein the actuation of the intraluminal catheter and the motion of the actuator is in one-to-one correspondence.

6. A catheter system comprising:
   a catheter having a distal end and a proximal end;
   a sheath having a distal end and a proximal end disposed over the catheter;
   a base connected at the proximal end of the catheter;
   an actuator disposed within the base and including a slider connected to the proximal end of the sheath and a pull which may be retracted or advanced, the pull having a plurality of ratcheting teeth and the slider being in direct ratcheting engagement with the plurality of ratcheting teeth; and
   a slot in the base configured to enable the slider to be disengaged from the ratcheting engagement with the plurality of ratcheting teeth,
   wherein retraction of the pull a certain distance retracts the sheath the same distance, yet advancement of the pull does not advance the sheath.

7. The catheter system of claim 6, further comprising:
   a self-expanding prosthesis disposed within the sheath configured to deploy as the sheath is retracted.

8. The catheter system of claim 6, further comprising:
   a top portion fixedly secured to the base and covering at least a portion of the actuator.

9. The catheter system of claim 6, further comprising:
   a spring mounted between the actuator and the base and configured to advance the actuator.

10. The catheter system of claim 6, further comprising:
    a locking mechanism to prevent motion of the actuator while locked.

11. The catheter system of claim 6, further comprising:
    an access port attached to the proximal end of the base wherein the access port accesses an inner lumen of the catheter.

12. An actuator for retracting a mechanism of an intraluminal catheter, comprising:
    a base;
    a handle slidably disposed on the base and including a plurality of proximal facing ratchet teeth; and
    a slider slidably disposed on the base and adapted to be connected to the mechanism of the intraluminal catheter, the slider including at least one distal facing ratchet tooth engaged with the plurality of proximal facing ratchet teeth of the handle, the slider being movable within the base in the same direction as the handle to actuate the mechanism of the intraluminal catheter, wherein the base includes a plurality of ratcheting teeth and at least one ratcheting tooth on the slider engages the plurality of ratcheting teeth on the base.

13. An actuator for retracting a mechanism of an intraluminal catheter, comprising:
   a base;
   a handle slidably disposed on the base and including a plurality of distal facing ratchet teeth; and
   a slider slidably disposed on the base and adapted to be connected to the mechanism of the intraluminal catheter, the slider including at least one proximal facing ratchet tooth engaged with the plurality of distal facing ratchet teeth of the handle, the slider being movable within the base in the same direction as the handle to actuate the mechanism of the intraluminal catheter, wherein the base includes a plurality of ratcheting teeth and at least one ratcheting tooth on the slider engages the plurality of ratcheting teeth on the base.

14. A device for actuating an intraluminal catheter, comprising:
   a handle base;
   an actuator slidably engaged with the handle base such that the actuator may be withdrawn or advanced; and
   a slider in ratcheted engagement with the actuator and adapted to be connected to an intraluminal catheter; and
   a slot disposed on the handle base for allowing visual observation of the position of the slider, the slot on the handle base is configured to enable the slider to be depressed to disengage the ratcheted engagement of actuator and the slider,
   wherein the ratcheted engagement between the actuator and slider allows the slider to be repeatedly withdrawn or advanced which actuates the catheter in a single direction.

15. A catheter system comprising:
   a catheter;
   a sheath disposed over the catheter;
   a base connected at the proximal end of the catheter;
   an actuator disposed within the base and including a slider connected to the proximal end of the sheath and having a pull which may be retracted or advanced, the pull having a plurality of ratcheting teeth attached thereto with the slider engaged with the plurality of ratcheting teeth, the base including a top portion which includes a plurality of ratcheting teeth and the slider includes at least one ratcheting tooth adapted to engage the plurality of ratcheting teeth of the top portion;
   wherein retraction of the pull a certain distance retracts the sheath the same distance, yet advancement of the pull does not advance the sheath.

16. The catheter system of claim 15, further comprising a slot on the top of the base configured to enable depressing the slider to disengage the ratcheting teeth engaging the top to the slider.

17. A catheter system comprising:
   a catheter;
   a sheath disposed over the catheter;
   a base connected at the proximal end of the catheter;
   an actuator disposed within the base and connected to the proximal end of the sheath and having a pull which may be retracted or advanced, a top portion fixedly secured to the base and covering at least a portion of the actuator, the top portion including a slot for allowing visual observation of the position of the actuator;
   wherein retracting the pull a certain distance retracts the sheath the same distance, yet advancing the pull does not advance the sheath.

18. A catheter system comprising:
   a catheter;
   a sheath disposed over the catheter;
   a base connected at the proximal end of the catheter;
   an actuator disposed within the base and connected to the proximal end of the sheath and having a pull which may be retracted or advanced, a spring mounted between the actuator and the base and biased in the direction of the retraction of the pull;
   wherein retracting the pull a certain distance retracts the sheath the same distance, yet advancing the pull does not advance the sheath.

19. An actuator for retracting a mechanism of an intraluminal catheter, comprising:
   a base;
   a handle slidably disposed on the base including a plurality of proximal facing ratchet teeth;
   a slider slidably disposed on the base and adapted to be connected to the mechanism of the intraluminal catheter including at least one distal facing ratchet tooth engaged with the plurality of proximal facing ratchet teeth of the handle;
   a cover connected to the base and covering at least portions of the handle and slider;
   a plurality of proximal facing ratchet teeth on the cover; and
   at least one distal facing ratchet tooth engaged with the plurality of proximal facing ratchet teeth on the cover.

20. An actuator for retracting a mechanism of an intraluminal catheter, comprising:
   a base;
   a handle slidably disposed on the base and including a plurality of distal facing ratchet teeth;
   a slider slidably disposed on the base and adapted to be connected to the mechanism of the intraluminal catheter, the slider including at least one proximal facing ratchet tooth engaged with the plurality of distal facing ratchet teeth of the handle;
   a cover connected to the base and covering at least portions of the handle and slider;
   a plurality of distal facing ratchet teeth on the cover; and
   at least one proximal facing ratchet tooth engaged with the plurality of distal facing ratchet teeth on the cover.

* * * * *